United States Patent
Chandy et al.

(10) Patent No.: US 9,878,006 B2
(45) Date of Patent: Jan. 30, 2018

(54) TREATMENT OF OBESITY AND OBESITY RELATED DISORDERS BY PHARMALOGICAL TARGETING OF KV1.3 POTASSIUM CHANNELS

(71) Applicants: The Regents of the University of California, Oakland, CA (US); Kineta One, LLC, Seattle, WA (US)

(72) Inventors: K. George Chandy, Laguna Beach, CA (US); Sanjeev Kumar Upadhayay, Irvine, CA (US); Ping H. Wang, Newport Coast, CA (US); Paolo Sassone-Corsi, Laguna Beach, CA (US); Kristin Lynn Eckel-Mahan, Irvine, CA (US); Shawn Iadonato, Seattle, WA (US); Jogesh Mukherjee, Irvine, CA (US); M. Reza Mirbolooki, Orange, CA (US)

(73) Assignees: THE REGENTS OF THE UNIVERSITY OF CALIFORNIA, Oakland, CA (US); KINETA ONE, LLC, Seattle, WA (US)

(*) Notice: Subject to any disclaimer, the term of this patent is extended or adjusted under 35 U.S.C. 154(b) by 0 days.

(21) Appl. No.: 15/049,353

(22) Filed: Feb. 22, 2016

(65) Prior Publication Data
US 2017/0095530 A1     Apr. 6, 2017

Related U.S. Application Data

(63) Continuation of application No. 14/347,602, filed as application No. PCT/US2012/058495 on Oct. 2, 2012, now abandoned.

(60) Provisional application No. 61/542,751, filed on Oct. 3, 2011.

(51) Int. Cl.
    *A61K 38/17* (2006.01)
(52) U.S. Cl.
    CPC .................. *A61K 38/1767* (2013.01)
(58) Field of Classification Search
    CPC .................................................. A61K 38/1767
    See application file for complete search history.

(56) References Cited

U.S. PATENT DOCUMENTS

| | | |
|---|---|---|
| 5,453,270 A | 9/1995 | Bills |
| 6,077,680 A | 6/2000 | Kem et al. |
| 6,451,336 B2 | 9/2002 | Sugano et al. |
| 6,616,944 B2 | 9/2003 | Kissel et al. |
| 6,861,405 B2 | 3/2005 | Desir et al. |
| 8,080,523 B2 | 12/2011 | Beeton et al. |
| 8,440,621 B2 | 5/2013 | Chandy et al. |
| 9,061,071 B2 | 6/2015 | Chandy et al. |
| 9,616,102 B2 | 4/2017 | Chandy et al. |
| 2003/0032595 A1 | 2/2003 | Desir et al. |
| 2007/0071764 A1 | 3/2007 | Sullivan et al. |
| 2008/0221024 A1 | 9/2008 | Chandy et al. |
| 2015/0072940 A1 | 3/2015 | Chandy et al. |

FOREIGN PATENT DOCUMENTS

| | | |
|---|---|---|
| EP | 1796709 | 6/2007 |
| EP | 2763702 | 8/2014 |
| EP | 3090753 | 11/2016 |
| WO | WO9823639 | 6/1998 |
| WO | WO9913895 | 3/1999 |
| WO | WO2006042151 | 4/2006 |
| WO | WO2007020286 | 2/2007 |
| WO | WO2010066840 | 6/2010 |

OTHER PUBLICATIONS

Seale et al. Brown Fat in Humans: Turning up the Heat on Obesity. Commentary. Diabetes, Jul. 2009. vol. 58, pp. 1482-1484.*
Albericio, F., et al., Convergent Peptide Synthesis; in Methods in Enzymol. Ed G. Fields, Academic Press, New York, NY, pp. 313-335.
Arch, J.R. The discovery of drugs for obesity, the metabolic effects of leptin and variable receptor pharmacology: perspectives from β3-adrenoceptor agonists. Naunyn-Schmiedeberg's Archives of Pharmacology. Aug. 2008, 378:225.
Barn, David R., et al., Synthesis of an array of amides by aluminium chloride assisted cleavage of resin-bound esters. Tetrahedron Letters, vol. 37, Issue 18, Apr. 29, 1996, pp. 3213-3216.97.
Bartelt, Alexander, et al., Brown adipose tissue activity controls triglyceride clearance. Nature Medicine, 2011, 17:200-205.
Beeton, C et al., Selective blockage of T lymphocyte K+ channels ameliorates experimental autoimmune encephalomyelitis experimental autoimmune encephalomyelitis, a model for multiple sclerosis, Proceedings of the National Academy of Sciences of USA, Nov. 20, 2001, pp. 13942-13947, vol. 98, No. 24, Washington, DC, US.
Beeton, C. et al., A Novel Fluorescent Toxin to Detect and Investigate Kv1.3 Channel Up-Regulation in Chronically Activated T Lymphocytes, J. Biol. Chem., vol. 278, No. 11, 9928-9937, Mar. 2003.
Beeton, C. et al., Targeting Effector Memory T Cells with a Selection Peptide Inhibitor of Kv1.3 Channels for Therapy of Autoimmune Diseases, Molecular Pharmacology, vol. 67, No. 4, 1369-, 2005.
Berendsen, H.J.C., A Glimpse of the Holy Grail? Science (1998) 282, pp. 642-643.

(Continued)

*Primary Examiner* — Marcela M Cordero Garcia
(74) *Attorney, Agent, or Firm* — Karen S Canady; canady + lortz LLP

(57) ABSTRACT

Activation of brown adipose tissue, treatment of obesity and/or treatment of obesity-related disorders in human or non-human animal subjects by administering to the subject a potassium channel inhibiting agent. The potassium channel inhibiting agent may comprise ShK toxin or a modified ShK toxin. Examples of modified ShK toxins include ShK-186.

20 Claims, 7 Drawing Sheets

(56) References Cited

OTHER PUBLICATIONS

Cannon, Barbara, and Jan Nedergaard. Brown Adipose Tissue: Function and Physiological Significance. Physiol Rev 84: 277-359, 2004; 10.1152/physrev.00015.2003.

Chandy, K. George, et al.; K+ channels as targets for specific immunomodulation, Trends in Pharmacological Sciences, May 1, 2004, pp. 280-289, vol. 25, No. 5, Elsevier, Hayworth, GB.

Clapham, John C., et al., Mice overexpressing human uncoupling protein-3 in skeletal muscle are hyperphagic and lean. Nature 406, 415-418 (Jul. 27, 2000).

Cypess, Aaron M., et al. Identification and Importance of Brown Adipose Tissue in Adult Humans. N Engl J Med 2009; 360:1509-1517Apr. 9, 2009. DOI: 10.1 056/NEJMoa0810780.

Degrado, W.F. and Kaiser, E.T., Solid-phase synthesis of protected peptides on a polymer-bound oxime: Preparation of segments comprising the sequence of a cytotoxic 26-peptide analogue. The Journal of Organic Chemistry 47(17), Aug. 1982.

Dulloo, A.G. The search for compounds that stimulate thermogenesis in obesity management: from pharmaceuticals to functional food ingredients. Obesity Reviews. vol. 12, Issue 10, Oct. 2011, pp. 866-883.

Nedergaard, J, et al., Unexpected evidence for active brown adipose tissue in adult humans. American Journal of Physiology-Endocrinology and Metabolism 293 (2), E444-E452.

Pappone, P.A. et al., Potassium channel block does not affect metabolic responses of brown fat cells. American Journal of Physiology—Cell Physiology Published Mar. 1, 1992 vol. 262 No. 3, C678-C681.

Pasut, G. and Veronese, F.M., Polymer—drug conjugation, recent achievements and general strategies. Progress in Polymer Science. vol. 32, Issues 8-9, Aug.-Sep. 2007, pp. 933-961.

Pennington et al. Structural Stabilization and Minimization of the Potassium Channel Blocker, ShK Toxin. Peptides 2000, pp. 155-156.

Pennington, et al., Chemical synthesis and characterization of ShK toxin: a potent potassium channel inhibitor from a sea anemone. Int. J Peptide Protein Res., 46, 354-358.

Rudinger. In: Peptide Hormones, JA Parsons, Ed. (1976), pp. 1-7.

Seydoux, J. et al., Dietary and pharmacological effectiveness of thermogenic stimulation in obesity treatment. In: Progress in Obesity Research 1990. Herausgegeben von Y. Oomura, S. Tarui, S. !none und T. Shimazu. 688 Seiten, zahlr. Abb. und Tab. John Libbey & Company Ltd., London 1991. pp. 135-144.

Sigma Genosys. Designing Custom Peptides. http://www.sigma-genosys.com/peptide.sub.--design.asp (Accessed Dec. 16, 2004), 2 pages.

Smilek, Dawn E., et al., A single amino acid change in a myelin basic protein peptide confers the capacity to prevent rather than induce experimental autoimmune encephalomyelitis. Proc Natl Acad Sci U S A. Nov. 1, 1991; 88(21): 3633-9637.

Soderlund, Veli, et al., Reduction of FDG uptake in brown adipose tissue in clinical patients by a single dose of propranolol. European Journal of Nuclear Medicine and Molecular Imaging. Jul. 2007, vol. 34, Issue 7, pp. 1018-1022.

Stewart, J.M., et al., Solid Phase Peptide Sythesis, 2nd Edition, Pierce Chemical Company, Rockford, III., 1984.

Suzuki, Takeshi, et al., Recent Advances in Fluorescent Labeling Techniques for Fluorescence Microscopy. Acta Histochemica Et Cytochemica. vol. 40 (2007) No. 5 p. 131-137.

Tatsumi, Mitsuaki, et al., Intense 18F-FDG Uptake in Brown Fat Can Be Reduced Pharmacologically. J Nucl Med Jul. 1, 2004 vol. 45 No. 7 1189-1193.

Van Marken Lichtenbelt, Wouter, et al., Cold-Activated Brown Adipose Tissue in Healthy Men. N Engl J Med 2009; 360:1500-1508. Apr. 9, 2009.

Virtanen, Kirsi A., et al., Functional Brown Adipose Tissue in Healthy Adults. N Engl J Med 2009; 360:1518-1525Apr. 9, 2009DOI: 10.1056/NEJMoa0808949.

Voet, D. and J.G. Voet. Biochemistry, 2nd Edition.(1995), pp. 235-241.

Wilken, J. et al., Chemical Protein Synthesis, Current Opin. Biotech., 9,412-426, 1998.

Xu, Jianchou, et al., The voltage-gated potassium channel Kv1.3 regulates peripheral insulin sensitivity. Proc Natl Acad Sci U S A. Mar. 2, 2004;101(9):3112-7. Epub Feb. 23, 2004.

European Search Report dated Sep. 10, 2009 in EP App. No. 05810512.3 (Publication No. EP1796709).

Extended European Search Report dated Sep. 6, 2016 in EP Application 16157419.9 (Publication No. EP3090753).

Supplementary European Search Report dated Mar. 4, 2015 in related EP App. No. 12838795.8 (Publication No. EP2763702).

International Search Report dated Feb. 25, 2013 in related application PCT/US2012/058495 (Publication No. WO2013052507).

Expert Committee on the Diagnosis and Classification of Diabetes Mellitus. Report of the expert committee on the diagnosis and classification of diabetes mellitus. Diabetes Care. Jan. 2003;26 Suppl 1:S5-20.

Farmer, Stephen R., Be Cool, Lose Weight. Nature 458, 839-840 (Apr. 16, 2009). doi:10.1038/458839a.

Hruby. Designing Peptide Receptor Agonists and Antagonists. Nature Reviews. Drug Discovery. Nov. 2002. vol. 1, pp. 847-858.

Jacobsson, H. et al., Reduction of FDG uptake in brown adipose tissue by propranolol. EurJ Nud Med Mol Imaging. Sep. 2005;32(9):1130.

Kalman, et al., ShK-Dap22, a Potent Kv1.3-specific Immunosuppressive Polypeptide, J. Biol Chem., 1998, vol. 273, No. 49, pp. 32697-32707.

King D.S., et al, 1990, A cleavage method which minimizes side reactions following Fmoc solid phase peptide synthesis. Int. J. Peptide Protein Res., 36, 255-266.

Lanigan, M.D. et al., Designed Peptide Analogues of the Potassium Channel Blocker ShK Toxin; Biochemistry, 25; 40 (51):15528-37, Dec. 2001.

Lucero, MT and Pappone, PA. Voltage-gated potassium channels in brown fat cells. J Gen Physiol. Mar. 1989;93 (3):451-72.

Manoil, Cohn and Traxler, Beth. Insertion of In-frame Sequence Tags into Proteins Using Transposons. Methods. vol. 20, Issue 1, Jan. 2000, pp. 55-61.

Merrifield, Bruce. Solid Phase Synthesis. Bioscience Reports. Nobel lecture, 8. Dec. 8, 1984. Rockefeller Univeriosity, New York, N.Y.

Messer, W.S., "Vasopressin and Oxytocin", web document updated Apr. 3, 2000; http://www.neurosci.pharm.utoledo.edu/MBC3320/vasopressin.htm; 5 pages.

\* cited by examiner

TREATMENT OF OBESITY AND OBESITY RELATED DISORDERS BY PHARMALOGICAL TARGETING OF KV1.3 POTASSIUM CHANNELS

RELATED APPLICATION

This patent application is a continuation of copending U.S. patent application Ser. No. 14/347,602 filed Mar. 26, 2014, which is a 35 U.S.C. § 371 national stage of PCT International Patent Application No. PCT/US12/58495 filed Oct. 2, 2012, which claims priority to U.S. Provisional Patent Application No. 61/542,751 filed Oct. 3, 2011, the entire disclosure of each such application being expressly incorporated herein by reference.

STATEMENT REGARDING GOVERNMENT SUPPORT

This invention was made with United States Government support under Grant Nos. NS48252, R43AI08569 and R01HL096987 awarded by the National Institutes of Health. The United States Government has certain rights in the invention.

FIELD OF THE INVENTION

The present invention relates generally to biology and medicine and more particularly to methods for treating obesity and obesity-related disorders.

BACKGROUND

Obesity is now a deadly global pandemic. The prevalence of overweight plus obesity among adults in USA in 2008 was 68% (~200 million people). Even a modest degree of obesity, particularly if the excess fat is located in the abdomen, increases the risks for type 2 diabetes mellitus, cardiovascular diseases, stroke and some forms of cancer. The economic cost of obesity is estimated to be $270 billion annually. Methods for managing body weight by dietary restriction and/or by exercise are largely ineffective as few people stick to dietary regimens for a long time, and compliance to regular exercise is equally poor. The result is generally a transient phase of weight loss (or weight stability) followed by a return on the trajectory towards obesity. These failures have highlighted the need for safe anti-obesity therapies.

In humans and many other mammals, fat is stored in adipose tissues. Adipose tissues are classified into two types-white adipose tissue (i.e., "white fat") and brown adipose tissue (i.e., "brown fat"). White fat stores calories as large lipid droplets within individual cells.[1] After food consumption, excess calories are stored as fat in white fat, which is mainly located under the skin of the buttocks and legs in women and around the internal organs in men. By contrast, brown fat stores little fat, instead burning it to produce heat and regulate body temperature.[1] Brown fat's ability to burn rather than store calories depends on each brown fat cell having many mitochondria. The mitochondria of brown fat cells are unique in that they contain UCP1, a protein that uncouples metabolism from ATP production in order to produce heat.[2] Small mammals and newborn humans have copious amounts of brown fat around their shoulder blades, which help them survive cold temperatures. Recent studies have conclusively identified brown fat in adult humans, mainly around the muscles of the lower neck and collarbone, as well as along the spine of the chest and abdomen.[3-5] The concept of managing obesity through the stimulation of thermogenesis in brown fat is currently a focus of considerable attention by the pharmaceutical, nutraceutical and functional food industries.[6] The skeletal muscle is another tissue involved in thermogenesis, and drugs that target thermogenesis by this tissue might also have value in the control of obesity.[6,7]

Brown fat is mainly enervated by the sympathetic nervous system. When hormonally activated, brown fat generates heat and burns excess energy. In experimental animals, thermogenesis in brown fat is controlled by norepinephrine released from the sympathetic nervous system; norepinephrine interacts mainly with β-adrenergic receptors to stimulate thermogenesis (FIG. 1).[2,8] Therefore, in rats, the β-adrenergic antagonist propranolol (5 mg/kg body wt) eliminates $^{18}$-fluoro-deoxyglucose uptake into brown fat.[8,9] In man, propranolol (1 mg/kg) has the same effect[10,11], clearly indicating that, also in man, glucose uptake (and thus probably thermogenesis) is under β-adrenergic control.

The idea of stimulating thermogenesis to manage or to assist in the management of obesity has a long history.[6] Thyroid extracts utilized in obesity therapy at the end of the 19th century induced marked reductions in body weight, but their use in obesity therapy fell into disrepute because of unacceptable side effects, including cardiac stimulation and increased protein catabolism.[6] Once the pivotal role of the sympatho-adrenal system in inducing thermogenesis in brown fat and skeletal muscle was understood, human trials in the 1990s evaluated all clinically-used sympathomimetic drugs for thermogenic anti-obesity properties.[12] However, the pharmaceutical companies were concerned about developing old drugs, many off patent-protection, as anti-obesity drugs. Around this time, the b3-adrenoceptors was reported to be the key receptor via which sympathetically released NA activated thermogenesis and fat oxidation in peripheral tissues, including the activation of UCP1 that mediates thermogenesis in brown fat. In rodents and dogs, several b3-adrenoceptor agonists were shown to have potent thermogenic anti-obesity effects—without producing the cardiovascular side effects associated with classical adrenoceptor stimulation.[13] The b3-adrenoceptors were demonstrated in human adipose tissue and skeletal muscle. However, these drugs either had poor selectivity for the human b3-adrenoceptor or poor oral availability, and no drug has progressed beyond phase II clinical trials.[13]

Parallel efforts to promote thermogenesis for treatment of obesity and obesity-related disorders have included phytotherapy (e.g. Ma Huang and Guarana), and food ingredients (methylxanthines, polyphenolic compounds, capsaicinoids and capsinoids, high protein diets and diets rich in long-chain unsaturated fatty acids). In this regard, U.S. Pat. No. 6,451,336 (Sugano, et al.) entitled Agent for Increasing Brown Fat Comprising Conjugated Linoleic Acid as Active Ingredient describes methods for stimulating production of brown adipose tissue by administering conjugated linoleic acid. Also, U.S. Pat. No. 5,453,270 (Bills) describes methods for increasing the amount of brown adipose tissue in a subject by administering to the subject a quantity of cultured brown adipose cells encapsulated in a semi-permeable membrane.

Besides pharmaceutical or nutritional approaches, it may be possible to stimulate brown fat activity by exposure to colder climates. In a 2009 study published in The *New England Journal of Medicine*, entitled "Identification and Importance of Brown Adipose Tissue in Adult Humans", the authors reported that brown fat activity decreased when the outdoor temperature was increased. Furthermore, a recent study in mice showed that short term exposure to cold accelerated plasma clearance of triglycerides as a result of increased uptake into brown fat, and in pathological conditions, cold exposure corrected hyperlipidemia.[14] These findings could be useful because individuals with metabolically active brown fat may be able to lose weight by exposure to cold. Weight loss might also be achieved through drugs that mimic the cold by activating the sympathetic nervous system.

Another possible use could be to take advantage of the correlation between brown fat and the finding that the zinc-finger protein PRDM16 is highly enriched in brown fat cells compared to white fat cells. A 2007 study found that the transgenic expression of PRDM16 at physiological levels in white fat depots stimulates the formation of brown fat cells, while depletion of PRDM16 through shRNA expression in brown fat cells causes a near total loss of the brown characteristics.

Both voltage-gated potassium channels (IKv) and calcium-activated potassium channels (IKca) are present in the cell membranes of brown adipose tissue cells. See, Lucero, M. T. et al.; Voltage-Gated Potassium Channels in Brown Fat Cells; J. Gen. Physiol. 93: 451-472 (1989). However, in prior studies using the potassium channel blocker tetraethylammonium (TEA), it was concluded that blockade of potassium channels in brown fat does not alter the metabolic response of brown adipose tissue cells to adrenergic stimulation. Pappone, P A., et al., Potassium Channel Block Does Not Affect Metabolic Responses of Brown Fat Cells; Am J Physiol. 262(3 Pt 1):C678-81 (1992).

Accordingly, there exists a need for the development of agents and methods to stimulate generation and activation of brown adipose tissue and/or skeletal muscle to promote weight loss and increase insulin sensitivity.

1. Stephen R. Farmer. Be cool, lose weight. *Nature* 458, 839-840, 2009
2. Cannon B, Nedergaard J. Brown adipose tissue: function and physiological significance. *Physiol Rev* 84: 277-359, 2004.
3. Virtanen, K. A. et al. *N. Eng. J. Med.* 360, 1518-1525, 2009.
4. van Marken Lichtenbelt, W. D. et al. *N. Eng. J. Med.* 360, 1500-1508, 2009.
5. Cypess, A. M. et al. *N. Eng. J. Med.* 360, 1509-1517, 2009.
6. Dulloo A G. The search for compounds that stimulate thermogenesis in obesity management: from pharmaceuticals to functional food ingredients. Obes. Rev. 12:866-883, 2011
7. Clapham J C et al. Mice overexpressing human uncoupling protein-3 in skeletal muscle are hyperphagic and lean. *Nature* 406:415-418,2000
8. Jan Nedergaard, Tore Bengtsson, and Barbara Cannon. Unexpected evidence for active brown adipose tissue in adult humans. Am J Physiol Endocrinol Metab 293:E444-E452, 2007.
9. Tatsumi M, Engles J M, Ishimori T, Nicely O, Cohade C, Wahl R L. Intense ([18])F-FDG uptake in brown fat can be reduced pharmacologically. *J Nucl Med* 45:1189-1193, 2004
10. Jacobsson H, Bruzelius M, Larsson S A. Reduction of FDG uptake in brown adipose tissue by propranolol. *Eur J Nucl Med Mol Imaging* 32: 1130, 2005.
11. Soderlund V, Larsson S A, Jacobsson H. Reduction of FGD uptake in brown adipose tissue in clinical patients by a single dose of propranolol. *Eur J Nucl Med Mol Imaging*. 34:1018-22, 2007.
12. Dulloo A G, Seydoux J, Girardier L. Dietary and pharmacological effectiveness of thermogenic stimulation in obesity treatment. In: Oomura Y, Tarui S, Inoue S, Shimazu T (eds). *Progress in Obesity Research* 1990. John Libbey & Company Ltd: London, 1990, pp. 135-144.
13. Arch J R. The discovery of drugs for obesity, the metabolic effects of leptin and variable receptor pharmacology: perspectives from beta3-adrenoceptor agonists. *Naunyn Schmiedebergs Arch Pharmacol;* 378: 225-240, 2008.
14. Bartell A. et al., Brown adipose tissue activity controls triglyceride clearance. Nature Medicine 17:200-5, 2011

SUMMARY OF THE INVENTION

The present invention provides methods for treatment of obesity and obesity-related disorders in a human or animal subject or patient by administration of a potassium channel inhibitor. The present invention also provides uses of potassium channel inhibiting agents in the treatment of obesity and obesity-related disorders.

Further in accordance with the present invention, there is provided a method for treating of obesity or an obesity-related disorder in a mammalian subject comprising the step of administering to the subject a therapeutically effective amount of a composition which inhibits potassium channels and thereby has an anti-obesity effect by increasing the activity of brown fat and/or skeletal muscle. In some embodiments, the composition may comprise one or more of potassium channel-inhibiting compositions described in United States Patent Application Publication No. 2008/0221024 (now issued as U.S. Pat. No. 8,080,523 (Chandy et al), the entire disclosure of which is expressly incorporated herein by reference. The potassium channel-inhibiting compositions described in United States Patent Application Publication No. 2008/0221024 generally comprise derivatives of the sea anemone toxin ShK. The known amino acid sequence of the ShK toxin is Arg-Ser-Cys-le-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys- Gly-Thr-Cys (SEQ ID NO: 1). The potassium channel-inhibiting compositions described in United States Patent Application Publication No. 2008/0221024 include those having the following sequences:

```
                                              (SEQ ID NO: 2)
p-phospho-Tyr-AEEAc-Arg-Ser-Cys-Ile-Asp-Thr-Ile- Pro-Lys-Ser-Arg-Cys-Thr-Ala-Phe-Gln-Cys-Lys-His- Ser-Met-Lys-Tyr-Arg-Leu-Ser-Phe-Cys-Arg-Lys-Thr- Cys-Gly-Thr-Cys;

(SEQ ID NO: 3)
p-phospho-Tyr-AEEAc-Arg-Ser-Cys-Ile-Asp-Thr-Ile-

Pro-Lys-Ser-Arg-Cys-Thr-Ala-Phe-Gln-Cys-Lys-His-

Ser-Met-Lys-Tyr-Arg-Leu-Ser-Phe-Cys-Arg-Lys-Thr-

Cys-Gly-Thr-Cys-amide;
```

```
                                            (SEQ ID NO: 4)
Tyr-AEEAc-Arg-Ser-Cys-Ile-Asp-Thr-Ile-Pro-Lys-

Ser-Arg-Cys-Thr-Ala-Phe-Gln-Cys-Lys-His-Ser-Met-

Lys-Tyr-Arg-Leu-Ser-Phe-Cys-Arg-Lys-Thr-Cys-Gly-

Thr-Cys-amide.

(SEQ ID NO: 5)
NH2-Arg-Ser-Cys-Ile-Asp-Thr-Ile-Pro-Lys-Ser-Arg-

Cys-Thr-Ala-Phe-Gln-Cys-Lys-His-Ser-Met-Lys-Tyr-

Arg-Leu-Ser-Phe-Cys-Arg-Lys-Thr-Cys-Gly-Thr-Cys-

X,
wherein X represents one of a carboxy-terminal
carboxyl or amide group.

(SEQ ID NO: 6)
NH2-Arg-Ser-Cys-Ile-Asp-Thr-Ile-Pro-Lys-Ser-Arg-

Cys-Thr-Ala-Phe-Arg-Cys-Lys-His-Ser-Met-Lys-Tyr-

Arg-Leu-Ser-Phe-Cys-Arg-Lys-Thr-Cys-Gly-Thr-Cys-

X,
wherein X represents one of a carboxy-terminal
carboxyl or amide group.

(SEQ ID NO: 7)
p-phospho-Tyr-AEEAc-Arg-Ser-Cys-Ile-Asp-Thr-Ile-

Pro-Lys-Ser-Arg-Cys-Thr-Ala-Phe-Arg-Cys-Lys-His-

Ser-Met-Lys-Tyr-Arg-Leu-Ser-Phe-Cys-Arg-Lys-Thr-

Cys-Gly-Thr-Cys-X,
wherein X represents one of a carboxy-terminal
carboxyl or amide group.
```

The present invention also provides uses of these particular potassium channel inhibiting compositions in the treatment of obesity and obesity-related disorders.

Still further in accordance with the present invention there are provided methods for treating obesity or obesity-related disorders in mammalian subjects by administering to the subject a therapeutically effective amount of a composition of matter that comprises ShK attached to an organic or inorganic chemical entity that has an anionic charge. The invention also includes uses of such compositions of matter for treating obesity or obesity-related disorders. These compositions of matter, the organic or inorganic chemical entity may be attached to the N-terminal residue of ShK. Examples of chemical entities having an anionic charge that may be attached to ShK include but are not necessarily limited to AEEAc-L-Tyr($PO_3H_2$), AEEAc-L-Pmp($OH_2$), AEEAc-D-Pmp($OH_2$), AEEAc-D-Pmp(OH, Et), AEEAc-L-Pmp($Et_2$), AEEAc-D-Pmp($Et_2$), AEEAc-L-Tyr, AEEAc-L-Phe(p-$NH_2$), AEEAc-L-Phe(p-$CO_2H$), AEEAc-L-Aspartate, AEEAc-D-Aspartate, AEEAc-L-Glutamate, or AEEAc-D-Glutamate.

Still further in accordance with the present invention, there are provided methods for, treating obesity or obesity-related disorders in mammalian subjects by administering to the subject a therapeutically effective amount of ShK(L5) as defined in Appendix A. ShK(L5) comprises ShK attached to AEEAc-L-Tyr($PO_3$ Hz)—i.e., SEQ ID NO: 2 above. The invention also includes uses of this composition (SEQ ID NO: 2) for treating obesity or obesity-related disorders. As used herein, the terms ShK(L5), ShK-186 and SEQ ID NO.: 2 are synonymous.

Still further in accordance with the present invention, the above-summarized compositions of matter are usable to attenuate body weight and/or body weight gain and are therefore useful for treatments of energy homeostasis and metabolism related (e.g. diabetes), food intake related and/or energy balance and body weight related diseases, disorders and/or conditions, including obesity and overweight, and diseases, disorders and/or conditions associated with obesity and/or overweight, such as type 2 diabetes and metabolic syndrome, in a patient in need thereof. The subject or patient may be a human or non-human animal.

They received vehicle (P6N) or ShK-186 (20, 100 or 500 μg/kg) on alternate days by subcutaneous injection. The weight is normalized to the average weight at the start of the study. All the mice in this study were males. Using repeated measures ANOVA, the p value <0.0001 for all the ShK-186 doses.

Figure 1A:
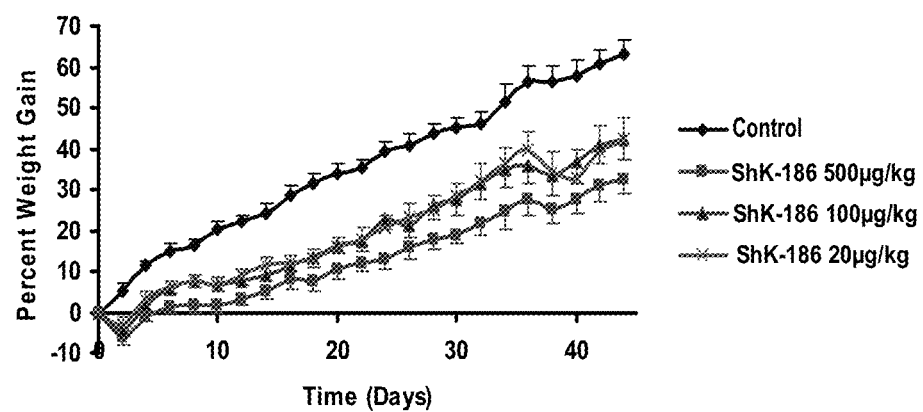
FIG. 1A is a graph of percent wait gain vs. time in a diet-induced obesity mouse model. All mice received the high fat/high fructose diet throughout the trial.
Figure 1B:
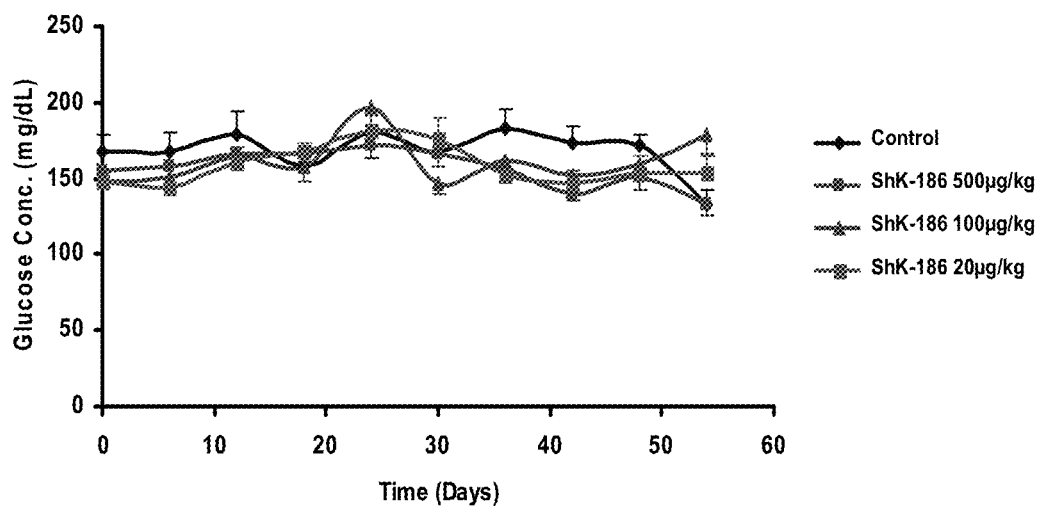

FIG. 1B is a graph of blood glucose concentration vs. time in the diet-induced obesity mouse model. All mice received the high fat/high fructose diet throughout the trial. They received vehicle (P6N) or ShK-186 (at 20, 100 or 500 μg/kg) on alternate days by subcutaneous injection. Blood glucose concentration was measured in each animal every six days.

Figure 2A:
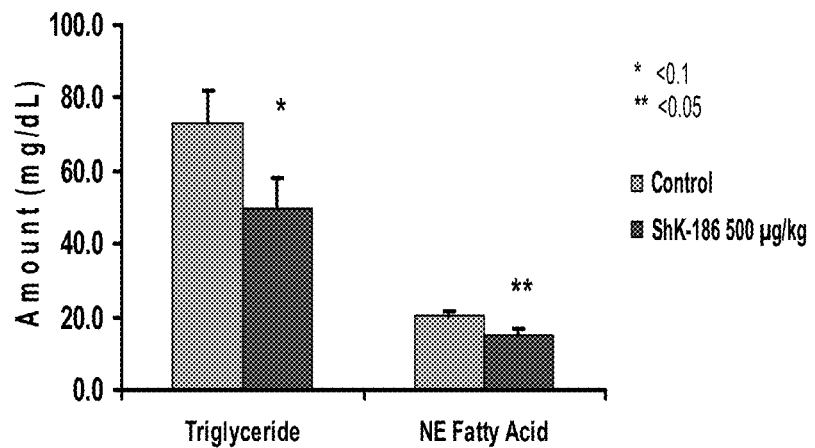
Figure 2B:
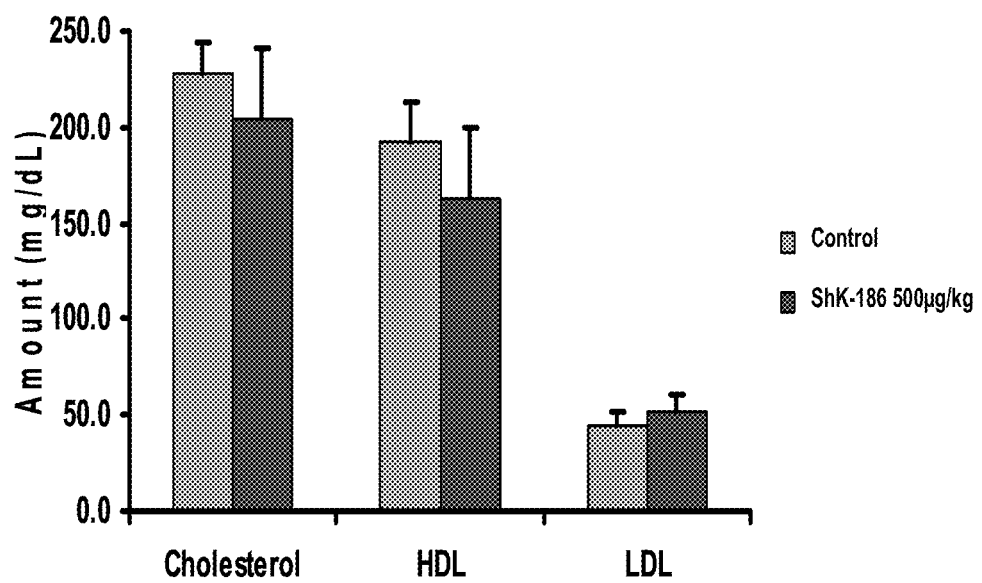

FIGS. 2A and 2B are bar graphs showing the lipid profiles in the diet-induced obesity model.

Figure 3A:
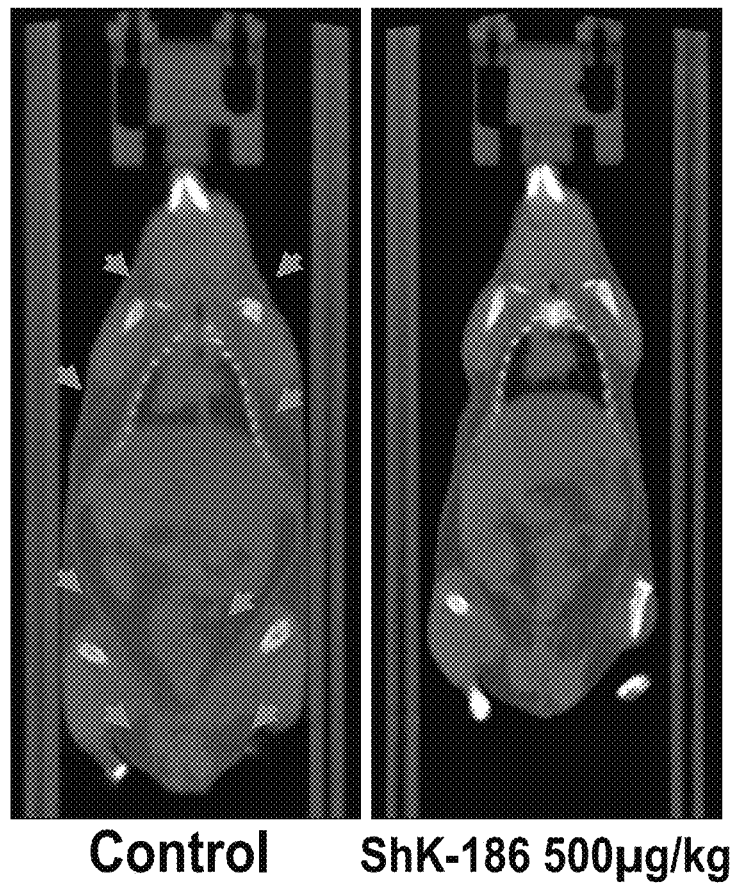

FIG. 3A shows CT scans of control and ShK-186-treated (500 μg/kg) mice after 45 days on a high fat/high fructose diet. White adipose tissue is highlighted by arrows.

Figure 3B:
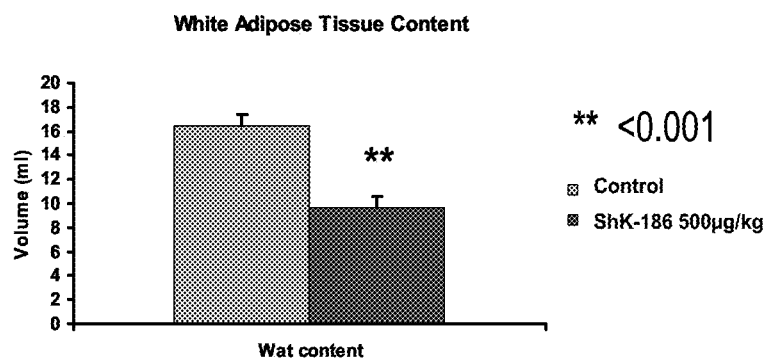
Figure 4A:
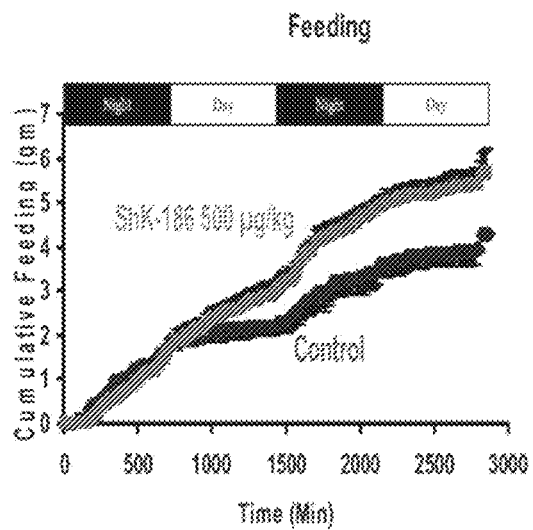
Figure 4B:
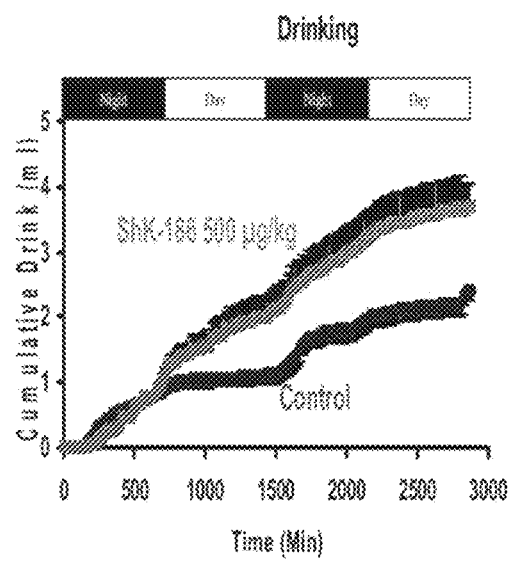
Figure 4C:
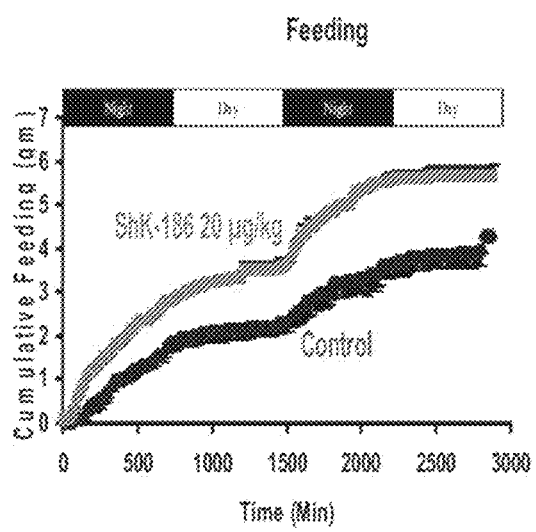
Figure 4D:
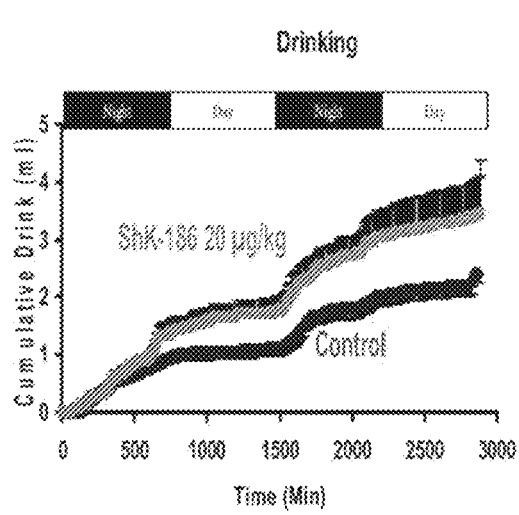
Figure 5A:
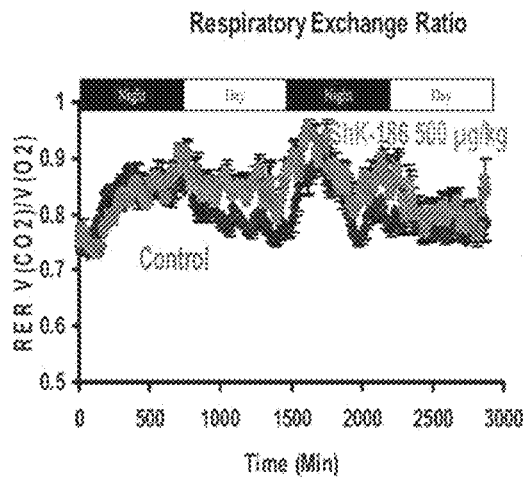
Figure 5B:
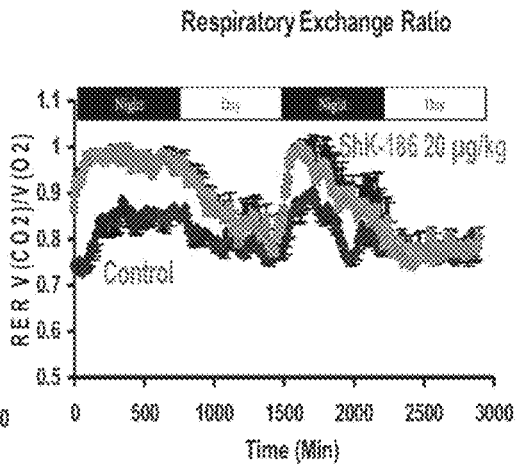
Figure 5C:
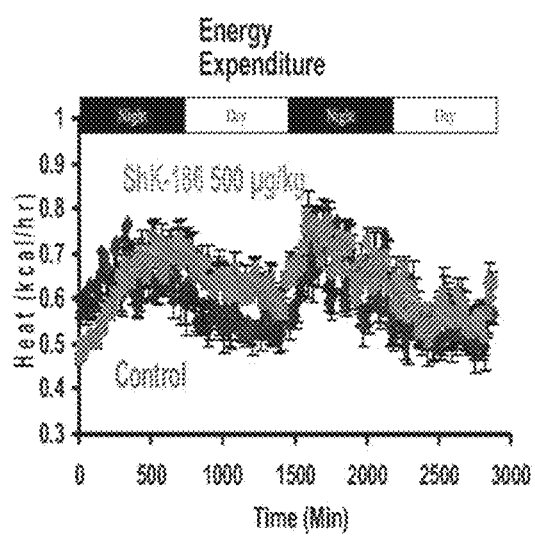
Figure 5D:
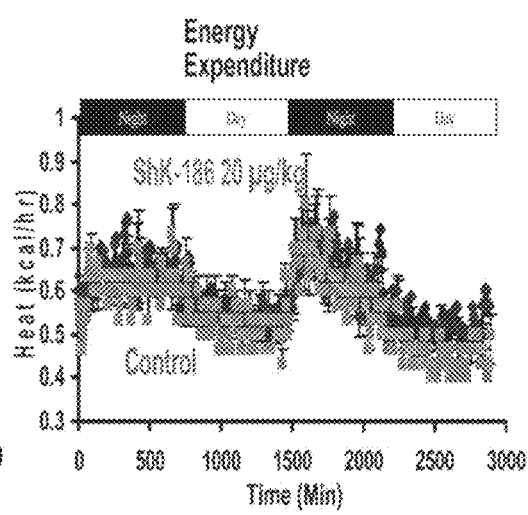

FIG. 3B is a bar graph comparing the white adipose tissue content of control m ice with that of mice receiving the 500 mg/kg dose of ShK-186.

FIGS. 4A through 4D show feeding and drinking patterns of mice analyzed in negative-flow CLAMS (Comprehensive Lab Animal Monitoring system) metabolic cages. All the animals were habituated with the high fat/high fructose diet for at least 7 days prior to the metabolic cage studies. All animals were placed individually in each metabolic cage and habituated for two days under normal 12 hr. light-dark cycle.

FIGS. 5A through 5D show Respiratory Exchange Ratio (RER) and energy expenditure in vehicle controls (n–2) and ShK-186-treated mice (n=2).

Figure 6A:
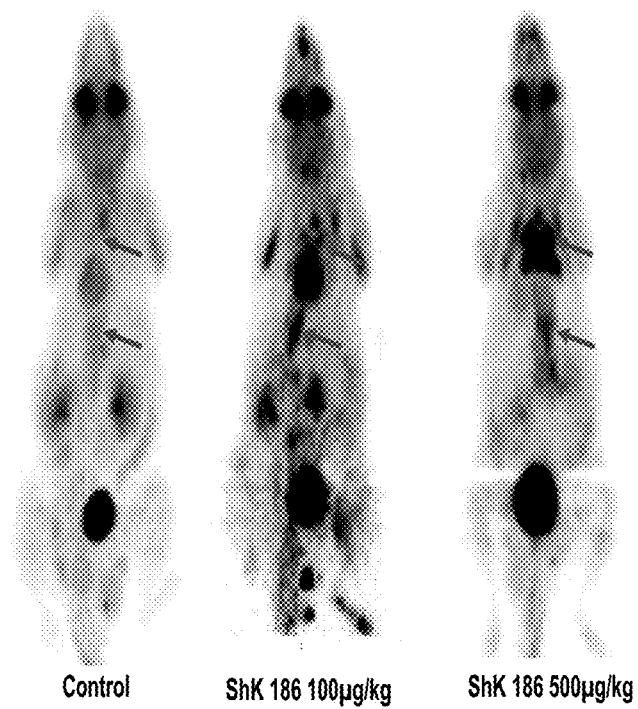
Figure 6B:
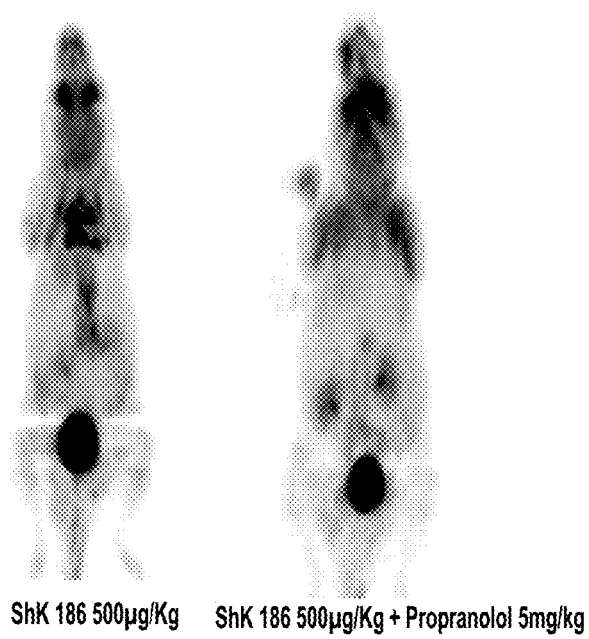

FIGS. 6A and 6B show PET scans with 18Fluoro-deoxyglucose ($^{18}$FDG). $^{18}$FDG uptake in brown adipose tissue is highlighted by arrows.

Figure 7:
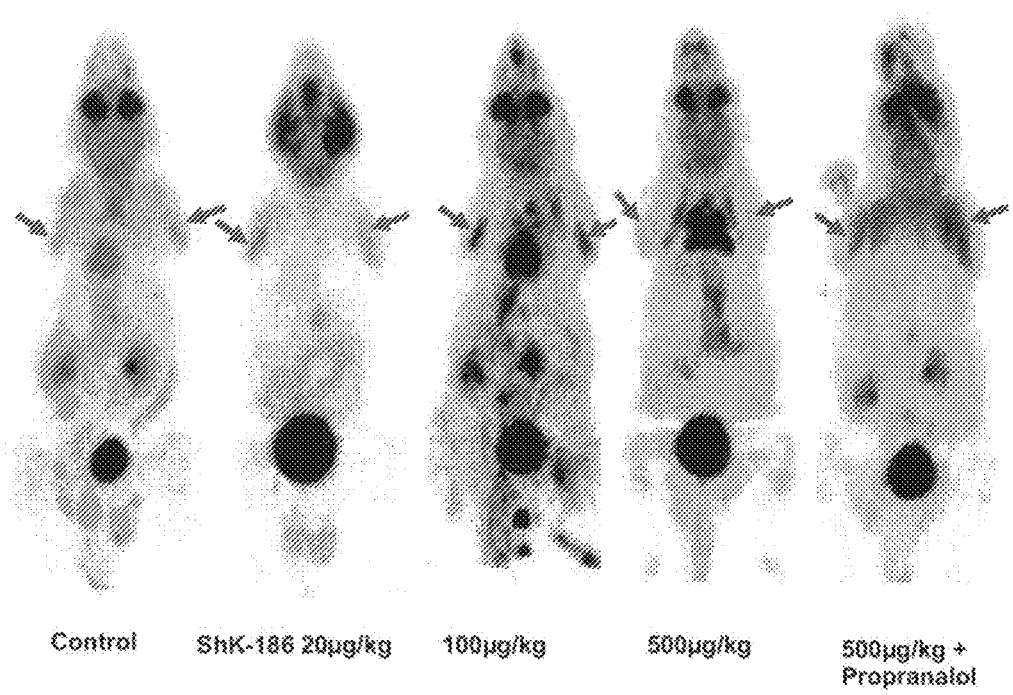

FIG. 7 shows PET imaging with $^{18}$FDG uptake by skeletal muscle highlighted by arrows.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

As used herein, the term "pharmacologically effective amount" (including "therapeutically effective amount") means an amount of a peptide according to the invention that is sufficient to induce a desired therapeutic or biological effect.

As used herein, the term "therapeutically effective amount" means the amount of a peptide of the invention that will elicit a biological or medical response in the mammal that is being treated by a medical doctor or other clinician.

As used herein, the term "prophylactically effective" or "preventive" means the amount of a peptide of the invention that will prevent or inhibit affliction or mitigate affliction of a mammal with a medical condition that a medical doctor or other clinician is trying to prevent, inhibit, or mitigate before a patient begins to suffer from the specified disease or disorder.

The term "diabetes" includes Type 1 Diabetes, which is insulin-dependent diabetes mellitus as diagnosed according to criteria published in the Report of the Expert Committee on the Diagnosis and Classification of Diabetes Mellitus {*Diabetes Care*, Vol. 24, Supp. 1, January 2001) whereby fasting plasma glucose level is greater than or equal to 126 milligrams per deciliter and for which the primary cause is pancreatic beta cell destruction, Type 2 Diabetes, which is non-insulin-dependent diabetes mellitus as diagnosed according to criteria published in the Report of the Expert Committee on the Diagnosis and Classification of Diabetes Mellitus whereby fasting plasma glucose level is greater than or equal to 126 milligrams per deciliter, and latent autoimmune diabetes mellitus of adults (LADA).

The term "metabolic syndrome" refers to metabolic disorders, particularly glucose and lipid regulatory disorders, including insulin resistance and defective secretion of insulin by pancreatic beta cells, and may further include conditions and states such as abdominal obesity, dyslipidemia, hypertension, glucose intolerance or a prothrombitic state, and which may further result in disorders such as hyperlipidemia, obesity, diabetes, insulin resistance, glucose intolerance, hyperglycemia, and hypertension.

The compositions and methods disclosed herein can be used for both medical applications and animal husbandry or veterinary applications. Typically, the methods are used in humans, but may also be used in other mammals. The term "patient" is intended to denote a mammalian individual, and is so used throughout the specification and in the claims.

The primary applications of the present invention involve human patients, but the present invention may be applied to laboratory, farm, zoo, wildlife, pet, sport or other animals.

Clinical indications and specific utilities include the following: obesity and metabolic syndrome; diseases, disorders and/or conditions involving energy homeostasis and metabolism (such as for example diabetes, in particular type 2 diabetes; dyslipidemia; fatty liver; hypercholesterolemia; hypertriglyceridemia; hyperuricacidemia; impaired glucose tolerance; impaired fasting glucose; insulin resistance syndrome; and metabolic syndrome); food intake (such as for example hyperphagia; binge eating; bulimia; and compulsive eating); and/or energy balance and body weight related diseases, disorders and/or conditions, more particularly such diseases, disorders and conditions characterized by excess body weight and/or excess food intake.

Peptides of the present invention are particularly believed to be useful for treatment of body weight related diseases, disorders and/or conditions characterized by excess body weight, including obesity and overweight (by promotion of weight loss, maintenance of weight loss, and/or prevention of weight gain, including medication-induced weight gain or weight gain subsequent to cessation of smoking), and diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

Peptides of the invention are particularly believed to be useful for treatment of obesity and type 2 diabetes, more specifically obesity. It will be understood that there are medically accepted definitions of obesity and overweight.

Subjects who are candidates for treatment by the present invention may be identified by, for example, measuring body mass index (BMI), which is calculated by dividing weight in kilograms by height in meters squared, and comparing the result with the definitions. The recommended classifications for BMI in humans, adopted by the Expert Panel on the Identification, Evaluation and Treatment of Overweight and Obesity in Adults, and endorsed by leading organizations of health professionals, are as follows: underweight <18.5 kg/m2, normal weight 18.5-24.9 kg/m2, overweight 25-29.9 kg/m2, obesity (class 1) 30-34.9 kg/m2, obesity (class 2) 35-39.9 kg/m2, extreme obesity (class 3) is 40 kg/m2 (Practical Guide to the Identification, Evaluation, and Treatment of Overweight and Obesity in Adults, The North American Association for the Study of Obesity (NAASO) and the National Heart, Lung and Blood Institute (NHLBI) 2000). Modifications of this classification may be used for specific ethnic groups and for children.

Another alternative for assessing overweight and obesity is by measuring waist circumference. There are several proposed classifications and differences in the cutoffs based on ethnic group. For instance, according to the classification from the International Diabetes Federation, men having waist circumferences above 94 cm (cut off for europids) and women having waist circumferences above 80 cm (cut off for europids) are at higher risk of diabetes, dyslipidemia, hypertension and cardiovascular diseases because of excess abdominal fat. Another classification is based on the recommendation from the Adult Treatment Panel III where the recommended cut-offs are 102 cm for men and 88 cm for women. However, the peptides of the invention may also be used for reduction of self-diagnosed overweight and for decreasing the risk of becoming obese due to life style, genetic considerations, heredity and/or other factors.

It is believed that peptides of invention upon administration to an animal, including man, will reduce body weight and/or body weight gain in that animal.

Combination Therapy for Certain Indications

The peptides, compositions and methods of the present invention may be used for treatment of any of the foregoing diseases, indications, conditions or syndromes, or any disease, indication, condition or syndrome by administration in combination with one or more other pharmaceutically active compounds. Such combination administration may be by means of a single dosage form which includes both a peptide of the present invention and one more other pharmaceutically active compound, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. Without meaning to limit combination therapies, the following exemplifies certain combination therapies which may be employed.

Mouse Obesity Model

The accompanying figures show the obesity-deterring efficacy of ShK-186 in the diet-induced obesity model in C57BL/J mice (diet composed of 21% fat+60% fructose-water). 8 week old C57BL/6 mice were purchased from Harlan Co. (Indianapolis, Ind.). They were fed a specialized high fat diet (#TD88137; 21% fat) purchased from Harlan Co. (Indianapolis, Ind.), and they received a 60% fructose solution to drink. The mice were administered vehicle (P6N) or ShK-186 (20, 100 or 500 µg/kg) by subcutaneous injections on alternate days. Animals were weighed on alternate days. Blood glucose levels were monitored every 6 days by tail-vein sampling using an Accu-Chek compact glucometer from Roche. The animal experimental protocol was approved by the Institutional Animal Care and Use Committee at University of California, Irvine.

Mice were fasted overnight before CT scans. All CT acquisitions were performed with an Inveon (Siemens Medical Solutions) preclinical CT scanner. During the scan 2% isoflurane was used and the mouse was laid in the supine position on the scanner. Images were reconstructed as 128× 128 matrices using a fast MAP algorithm with a smoothing factor of 0.1. CT HU of WAT was obtained by calibrating the CT data using linear interpolation of water CT Density (CT HU=0) and air CT density (CT HU=−1000). After the scan procedure, animals were allowed to recover from anesthesia, placed in their cages and monitored for normal recovery. All scanning data was acquired in full list mode and sorted into a single frame, 3 dimensional sinogram, which was rebinned using a Fourier rebinning algorithm. The images were reconstructed using 2 dimensional filter back projection using a Hanning Filter with a Nyquist cut off at 0.5, and corrected for attenuation using the Co-57 attenuation scan data. All CT Data analysis was done using PMOD 3.0 software.

$^{18}$F-FDG was purchased from PETNET. Mice were fasted overnight before CT or PET scan. For PET scan animals were injected with 0.1-0.2 mCi of $^{18}$F-FDG in sterile saline. Approximately, 0.02 to 0.05 ml was administered intravenously (tail vein) under 2% Isoflurane and animal was allowed to remain awake for 60 mins in their cages to allow distribution and uptake of $^{18}$F-FDG. During the scan 2% isoflurane was used and the mouse was laid in the supine position on the scanner. All PET acquisitions were performed with an Inveon (Siemens Medical Solutions) preclinical PET scanner. PET data was acquired for 30 min. When used with PET scanner CT data was obtained immediately after PET imaging without changing the position of the animal. PET images were corrected for attenuation, scatter, randoms, and dead time. Images were reconstructed as 128×128 matrices using a fast MAP algorithm with a smoothing factor of 0.1. CT HU of BAT and WAT was obtained by calibrating the CT data using linear interpolation of water CT Density (CT HU=0) and air CT density (CT HU=−1000). After the scan procedure, animals were allowed to recover from anesthesia, placed in their cages and monitored for normal recovery.

All scanning data was acquired in full list mode and sorted into a single frame, 3 dimensional sinogram, which was rebinned using a Fourier rebinning algorithm. The images were reconstructed using 2 dimensional filter back projection using a Hanning Filter with a Nyquist cut off at 0.5, and corrected for attenuation using the Co-57 attenuation scan data. All MicroPET and CT Data analysis was done using PMOD 3.0 software.

All mice received the high fat/high fructose diet throughout the trial. They received vehicle (P6N) or ShK-186 (20, 100 or 500 µg/kg) on alternate days by subcutaneous injection. The weight is normalized to the average weight at the start of the study. All the mice in this study were males. Using repeated measures ANOVA, the p value <0.0001 for all the ShK-186 doses.

As shown in FIG. 1A, ShK-186 administered by subcutaneous administration on alternate days significantly reduced weight gain (p value <0.0001 for all the ShK-186 doses) in a dose-dependent manner compared to vehicle-treated mice. Also, this reduction in weight gain occurred without changing blood glucose levels, as shown by FIG. 1B.

FIG. 2A shows triglyceride and non-esterified fatty acid levels in plasma. FIG. 2B shows cholesterol, HLD and LDL in plasma. Blood was drawn by cardiac puncture in heparin tubes and plasma separated and stored at −20° C. Lipid levels in the plasma were analyzed at the Comparative Pathology Laboratory at the University of California Davis using the Roche Diagnostics COBAS INTEGRA 400 Plus using manufacturer's recommendations. p value=0.01325, NEFA; p<0.05, triglyceride.

As highlighted by arrows in FIG. 3A and as shown in the bar graph of FIG. 3B, ShK-186-treatment significantly reduced the volume of white adipose tissue in the diet-induced obesity model compared to vehicle-treated mice (p=0.000708).

FIG. 4A through 4D shows feeding and drinking by mice administered vehicle (control) or ShK-186 at the onset of the measuring phase. p<0.05 after first 24 hrs in all graphs. Mice were acclimated for 2 days in the metabolic cages before the measurements were made. Control mice feed and drink during the dark-cycle and "rest" during the light-cycle, whereas ShK-186-treated mice feed and drink during both dark and light cycles.

FIGS. 5A through 5D show Respiratory Exchange Ratio (RER) and energy expenditure in vehicle controls (n-2) and ShK-186-treated mice (n=2). RER of 0.70 is when a subject is metabolizing pure fat, whereas RER of 1.0 is when a subject is metabolizing pure carbohydrate. ShK-186-treated mice metabolize more carbohydrate than fat, especially during the light cycle. ShK-186-treated mice have greater energy expenditure during the day, but are roughly equivalent energy expenditure during the night.

FIGS. 6A and 6B show PET scans with 18Fluoro-deoxyglucose ($^{18}$FDG) uptake in brown adipose tissue highlighted by arrows. FIG. 6A shows that ShK-186 (at 100 and 500 µg/kg) induces $^{18}$FDG-uptake by brown adipose tissue. FIG. 6B shows that $^{18}$FDG uptake by brown adipose tissue is inhibited by propranolol (5 m/kg).

FIG. 7 shows PET imaging with $^{18}$FDG uptake by skeletal muscle highlighted by arrows. ShK-186 (at 20, 100 and 500 µg/kg) increased $^{18}$FDG uptake by skeletal muscle but propranolol (5 mg/kg) did not inhibit this uptake. PET scanning was performed in the same manner as in relation to FIG. 6.

Combination Therapy for Obesity and Related Metabolic Syndrome.

One or more peptides of the invention may be combined with one or more other pharmacologically active agent (s) that is (are) useful in the treatment of various weight and feeding-related disorders, such as obesity and/or overweight, in particular other anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioral therapy in weight reduction programs.

Generally, a total dosage of the below-described obesity control agents or medications, when used in combination with one or more peptides of the present invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

One or more peptides of the invention may be combined with one or more other pharmacologically active agent (s) that is (are) useful in the treatment of diabetes, such as other anti-diabetic drugs.

One or more peptides of the invention may in addition or alternatively further be combined with one or more other pharmacologically active agent(s) that is (are) useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

According to a further aspect of the invention there is provided a combination treatment comprising the administration of a pharmacologically effective amount of a peptide according to the invention, or a pharmaceutically acceptable salt thereof, optionally together with a pharmaceutically acceptable diluent or carrier, with the simultaneous, sequential or separate administration of one or more of the following agents selected from: (1) insulin and insulin analogues; (2) insulin secretagogues, including sulphonylureas (e.g. glipizide) and prandial glucose regulators (sometimes called "short-acting secretagogues"), such as meglitinides (e.g. repaglinide and nateglinide); (3) agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide); (4) insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity; (5) agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators; (6) agents designed to reduce/slow the absorption of glucose from the intestine, such as alpha-glucosidase inhibitors (e.g. miglitol and acarbose); and (7) agents which antagonise the actions of or reduce secretion of glucagon, such as amylin analogues (e.g. pramlintide); (7) agents that prevent the reabsorption of glucose by the kidney, such as sodium-dependent glucose transporter 2 (SGLT-2) inhibitors (e.g. dapagliflozin); (8) agents designed to treat the complications of prolonged hyperglycaemia, such as aldose reductase inhibitors (e.g. epalrestat and ranirestat); and agents used to treat complications related to micro-angiopathies; (9) anti-dyslipidemia agents, such as HMG-CoA reductase inhibitors (statins, e.g. rosuvastatin) and other cholesterol-lowering agents; PPARα agonists (fibrates, e.g. gemfibrozil and fenofibrate); bile acid sequestrants (e.g. cholestyramine); (10) cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants, such as probucol; and omega-3 fatty acids; (11) antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem); angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide); (12) haemostasis modulators, including antithrombotics, such as activators of fibrinolysis; thrombin antagonists; factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole); (14) anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant); (15) feeding behavior modifying agents, such as orexin receptor modulators and melanin-concentrating hormone (MCH) modulators; (16) glucagon like peptide-1 (GLP-1) receptor modulators; (17) neuropeptideY (NPY)/NPY receptor modulators; (18) pyruvate dehydrogenase kinase (PDK) modulators; (19) serotonin receptor modulators; (20) leptin/leptin receptor modulators; (21) ghrelin/ghrelin receptor modulators; or (22) monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

According to an additional further aspect of the present invention there is provided a combination treatment comprising the administration of a pharmacologically effective amount of a compound according to the invention, or a pharmaceutically acceptable salt thereof, optionally together with a pharmaceutically acceptable carrier, with the simultaneous, sequential or separate administration of very low calorie diets (VLCD) or low-calorie diets (LCD).

Methods of Making Peptides

In general, the peptides of the present invention may be synthesized by solid-phase synthesis and purified according to methods known in the art. Any of a number of well-known procedures utilizing a variety of resins and reagents may be used to prepare the peptides of the present invention. In such methods the synthesis of peptides of the invention can be carried out by sequentially incorporating the desired amino acid residues one at a time into the growing peptide chain according to the general principles of solid phase methods. These methods are disclosed in numerous references, including Merrifield, R. B., Solid phase synthesis (Nobel lecture). *Angew Chem* 24:799-810 (1985) and Barany et al., The Peptides, Analysis, Synthesis and Biology, Vol. 2, Gross, E. and Meienhofer, J., Eds. Academic Press 1-284 (1980). In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods. Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethanetype protecting groups, such as t-butyloxycarbonyl (Boc), diisopropylmethoxycarbonyl, isopropoxycarbonyl, and allyloxycarbonyl (Alloc). Fmoc are preferred for alpha amino protection. Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arginine.

Solid phase synthesis is commenced from the C-terminal end of the peptide by coupling a protected alpha amino acid to a suitable resin. Such starting material is prepared by attaching an alpha amino-protected amino acid by an amide linkage to a 4-(2', 4'-dimethoxylphenyl-aminomethyl-phenoxy (Rink Amide) resin, a 4-(2',4'-dimethoxylphenyl-aminomethyl)-phenoxyacetamido-norleucyl-MBHA resin, an amino-xanthen-3-yloxy-merifiel resin (Sieber Amide) resin, or by an ester linkage to a p-benzyloxybenzyl alcohol (Wang) resin, a 2-chlorotrityl chloride resin or by other means well known in the art. Fmoc-Linker-BHA resin supports are commercially available and generally used when feasible. The resins are carried through repetitive cycles as necessary to add amino acids sequentially.

The alpha amino Fmoc protecting groups are removed under basic conditions. Piperidine, piperazine, diethylamine, or morpholine (20-40% v/v) in N,Ndimethylformamide (DMF) may be used for this purpose. Following removal of the alpha amino protecting group, the subsequent protected amino acids are coupled stepwise in the desired order to obtain an intermediate, protected peptide-resin.

The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin.

Finally, peptides can be modified at their N-terminus to obtain several of the preferred embodiments of the application including by addition of AEEAc-L-Tyr($PO_3H_2$), AEEAc-L-Pmp($OH_2$), AEEAc-D-Pmp($OH_2$), AEEAc-D-Pmp(OH, Et), AEEAc-L-Pmp($Et_2$), AEEAc-D-Pmp($Et_2$), AEEAc-L-Tyr, AEEAc-L-Phe(p-$NH_2$), AEEAc-L-Phe(p-$CO_2H$), AEEAc-L-Aspartate, AEEAc-D-Aspartate, AEEAc-L-Glutamate, or AEEAc-D-Glutamate.

Peptides of the present invention can be cyclized by air oxidation or using a glutathione exchange system following cleavage of the crude peptide from the resin. A variety of specific cyclization methods are known in the art. Cyclized peptide can be purified by reverse phase high performance liquid chromatography (RP-HPLC), using a suitable column, such as a C18 column, or other methods of separation or purification, such as methods based on the size or charge of the peptide, can also be employed. Once purified, the peptide can be characterized by any number of methods, such as high performance liquid chromatography (HPLC), amino acid analysis, mass spectrometry, and the like.

For peptides of the present invention which have a C-terminus substituted amide derivative or N-alkyl group, synthesis may proceed by solid phase synthesis commenced from the C-terminal end of the peptide by coupling a protected alpha amino acid to a suitable resin. Such methods for preparing substituted amide derivatives on solid-phase have been described in the art. See, for example, Bam D. R. et al., Synthesis of an array of amides by aluminum chloride assisted cleavage on resin bound esters. *Tetrahedron Letters*, 37:3213-3216 (1996); DeGrado W. F. and Kaiser E. T., Solidphase synthesis of protected peptides on a polymer bound oxime: Preparation of segments comprising the sequences of a cytotoxic 26-peptide analogue. *J. Org. Chem.*, 47:32583261 (1982).

While synthesis has been described primarily with reference to solid phase Fmoc chemistry, it is to be understood that other chemistries and synthetic methods may be employed to make the cyclic peptides of the invention, such as by way of example and not limitation, methods employing Boc chemistry, solution chemistry, and other chemistries and synthetic methods.

It shall be understood that as used herein all references to peptides according to the invention, including a specific chemical formula or name, are intended to include all pharmaceutically acceptable salts, solvates, hydrates, polymorphs, prodrugs, metabolites, stereoisomers, and tautomeric isomers thereof.

Peptides of the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids (see "Handbook of Pharmaceutical Salts: Properties, Selection and Use", P. H. Stahl, P. G. Wermuth, IUPAC, Wiley-VCH, 2002). Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of peptides of the present invention are prepared in a suitable solvent for the peptide and an excess of an acid, such as hydrochloric, hydrobromic, sulfuric, phosphoric, acetic, trifluoroacetic (TFA), citric, tartaric, maleic, succinic or methanesulfonic acid. The acetate, ammonium acetate and TFA acid salt forms are especially useful.

Pharmaceutical Compositions.

The invention provides a pharmaceutical composition that includes one or more peptides of the present invention and a pharmaceutically acceptable carrier. When formulated with a pharmaceutically acceptable carrier, the compound of the invention may be present in the pharmaceutical composition in a concentration from 0.0001 to 99.5%, such as from 0.001 to 95%, by weight of the total composition. The choice of carrier is within the knowledge of a person skilled in the art and depends on, for instance, the mode of administration, the dosage form, and the physical properties of the active compound, such as solubility and stability. The term "carrier" as used herein relates to a therapeutically inactive ingredient. The dosage form may be a solid, semi-solid, liquid or self-gelling system. The formulation may be an immediate and/or modified release, including delayed-, sustained-, pulsed-, controlled-, targeted and programmed release formulation. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Formulation excipients may include polyvinylpyrrolidone, gelatin, hydroxy propyl cellulose (HPC), acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. A preferred embodiment includes a liquid formulation containing 1, 10, or 25 mg/mL peptide in a solution composed of 10 mM sodium phosphate, 0.8% (w/v) NaCl, 0.05% (w/v) polysorbate 20, in water for injection (pH 6).

For solid administration formulations, any of a variety of thickening, filler, bulking and carrier additives may be employed, such as starches, sugars, cellulose derivatives, fatty acids and the like. For topical administration formulations, any of a variety of creams, ointments, gels, lotions and the like may be employed.

For most pharmaceutical formulations, non-active ingredients will constitute the greater part, by weight or volume, of the preparation. For pharmaceutical formulations, it is also contemplated that any of a variety of measured-release, slow-release or sustained-release formulations and additives may be employed, so that the dosage may be formulated so as to provide delivery of a peptide of the present invention over a period of time. In general, the actual quantity of peptides of the present invention administered to a patient will vary between fairly wide ranges depending on the mode of administration, the formulation used, and the response desired. In practical use, the peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like.

In preparing the compositions for an oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another dosage unit form, sublingual constructs may be employed, such as sheets, wafers, tablets or the like.

The tablets, pills, capsules, and the like may also contain a binder such as povidone, gum tragacanth, acacia, corn starch or gelatin; diluents; fillers such as microcrystalline cellulose; excipients such as dicalcium phosphate; a disintegrating agent such as corn starch, potato starch or alginic acid; preservatives; colorants; a lubricant such as magnesium stearate; and a sweetening agent such as sucrose, lactose or saccharin. When a dosage unit form is a capsule, it may contain, in addition to materials of the above type, a liquid carrier such as fatty oil. Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

If formulated for oral delivery, the peptide is preferably formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will disintegrate after passing through the stomach to release the active drug substance. Materials that may be used includes cellulose acetate phthalate, hydroxypropylmethylethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach, and may be selected such that the enteric coating dissolves at a pH of approximately at least 5.5, more preferable at a pH of from about 6.0 to about 8.0.

Any of a variety of permeation enhancers may be employed, to increase uptake in the intestines upon dissolution of the enteric coating. In one aspect, permeation enhancers increase either paracellular or transcellular transport systems.

Representative, non-limiting examples of such permeation enhancers include calcium chelators, bile salts (such as sodium cholate), and fatty acids. In some embodiments, peptides or polypeptides that act as substrates for intestinal proteases are further added. Peptides may also be administered parenterally. Solutions or suspensions of these active peptides may for instance be prepared in water mixed with for instance hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The peptides of the present invention may be therapeutically applied by means of nasal administration. By "nasal administration" is meant any form of intranasal administration of any of the cyclic peptides of the present invention. The peptides may be in an aqueous solution, such as a solution including saline, citrate or other common excipients or preservatives. The peptides may also be in a dry or powder formulation.

If in an aqueous solution, the peptides may be appropriately buffered by means of saline, acetate, phosphate, citrate, acetate or other buffering agents, which may be at any physiologically acceptable pH, such as from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, peptides of the present invention may be administered directly into the lung. Intrapulmonary administration may be performed by means of a metered dose inhaler, a device allowing self-administration of a metered bolus of a peptide of the present invention when actuated by a patient during inspiration. Any of a variety of different techniques may be used to make dry powder microparticles, including but not limited to micro-milling, spray drying and a quick freeze aerosol followed by lyophilization.

The peptides of the present invention may be therapeutically administered by means of an injection of a sustained release formulation. In general, any of a number of injectable and bioerodible polymers may be employed in a sustained release injectable formulation. Alternatively other sustained release formulations may be employed, including formulations permitting subcutaneous injection, which other formulations may include one or more of nano/microspheres, liposomes, emulsions (such as water-in-oil emulsions), gels, insoluble salts or suspensions in oil The formulation may be such that an injection is required on a daily, weekly, monthly or other periodic basis, depending on the concentration and amount of peptide, the sustained release rate of the materials employed, and other factors known to those of skill in the art.

Routes of Administration.

If a composition including one or more peptides of the present invention is administered by injection, the injection may be intravenous, subcutaneous, intramuscular, intraperitoneal or other means known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount.

In general, the actual quantity of peptide of the present invention administered to a patient will vary between fairly wide ranges depending upon the mode of administration, the patient (including weight, sex, health condition and diet), the formulation used, and the response desired. The dosage for treatment is administration, by any of the foregoing means or any other means known in the art, of an amount sufficient to bring about the desired therapeutic effect. The peptides of the present invention are highly active. For example, the peptide can be administered (as a single dose or in divided daily doses) at about 0.001, 0.01, 0.5, 1, 5, 50, 100, 500, 1000, 5000, 10000, or 25000 ug/kg body weight, depending on the specific peptide selected, the desired therapeutic response, the route of administration, the formulation and other factors known to those of skill in the art.

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo. Prodrugs are any covalently bonded compounds, which release the active parent peptide drug in vivo. Conventional procedures for the selection and preparation of suitable prodrug derivatives are described, for example, in "Design of Prodrugs", ed. H. Bundgaard, Elsevier, 1985.

Certain modifications of peptides of the present invention may be made in order to enhance the half-life of the peptide (see G. Pasuta and F. M. Veronese (2007) "Polymer-drug conjugation, recent achievements and general strategies" *Progress in Polymer Science* 32 (8-9): 933-961).

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A method for activation of brown adipose tissue in a human or animal subject, said method comprising the steps of administering to a subject in need of treatment for hyperphagia, hyperlipidemia, dyslipidemia, hyperglycemia, or hypercholesteremia, an agent which inhibits potassium channels, wherein the agent comprises an ShK toxin attached to a chemical entity, wherein the chemical entity attached to the Shk toxin is selected from: AEEAc-L-Tyr (PO3H2), AEEAc-L-Pmp(OH2), AEEAc-D-Pmp(OH2), AEEAc-D-Pmp(OH, Et), AEEAc-L-Pmp(Et2), AEEAc-D-Pmp(Et2), AEEAc-L-Tyr, AEEAc-L-Phe(p-NH2), AEEAc-L-Phe(p-CO2H), AEEAc-L-Aspartate, AEEAc-D-Aspartate, AEEAc-L-Glutamate, and AEEAc-D-Glutamate.

2. The method according to claim 1 wherein the agent comprises the ShK toxin of SEQ ID NO:1.

3. The method according to claim 1 wherein the agent comprises the Shk toxin selected from: SEQ ID NO: 2, SEQ ID NO: 3, SEQ ID NO:4, SEQ ID NO:5, SEQ ID NO:6 or SEQ ID NO:7.

4. The method according to claim 1 wherein said chemical entity is attached to the N-terminal residue of ShK.

5. The method according to claim 1 wherein the ShK toxin is obtained from a natural source.

6. The method according to claim 1 wherein the ShK toxin is synthetic.

7. The method according to claim 1 wherein the chemical entity includes a fluorophore tag.

8. The method according to claim 1 wherein the chemical entity attached to ShK toxin comprises AEEAc-L-Pmp (OH2).

9. The method according to claim 1 wherein the chemical entity attached to ShK toxin comprises AEEAc-D-Pmp (OH2).

10. The method according to claim 1 wherein the chemical entity attached to ShK toxin comprises AEEAc-D-Pmp (OH, Et).

11. The method according to claim 1 wherein the chemical entity attached to ShK toxin comprises AEEAc-L-Pmp (Et2).

12. The method according to claim 1 wherein the chemical entity attached to ShK toxin comprises AEEAc-D-Pmp (Et2).

13. The method according to claim 1 wherein the chemical entity attached to ShK toxin comprises AEEAc-L-Tyr.

14. The method according to claim 1 wherein the chemical entity attached to ShK toxin comprises AEEAc-L-Phe (p-NH2).

15. The method according to claim 1 wherein the chemical entity attached to ShK toxin comprises AEEAc-L-Phe (p-CO2H).

16. The method according to claim 1 wherein the chemical entity attached to ShK toxin comprises AEEAc-L-Aspartate.

17. The method according to claim 1 wherein the chemical entity attached to ShK toxin comprises AEEAc-D-Aspartate.

18. The method according to claim 1 wherein the chemical entity attached to ShK toxin comprises AEEAc-L-Glutamate.

19. The method of claim 1, wherein the agent is administered at a dose of about 0.001 to about 1000 µg/kg body weight per day.

20. The method of claim 19, wherein the agent is administered at a dose of about 0.001 to about 500 µg/kg body weight per day.

* * * * *

UNITED STATES PATENT AND TRADEMARK OFFICE
CERTIFICATE OF CORRECTION

PATENT NO.       : 9,878,006 B2
APPLICATION NO.  : 15/049353
DATED            : January 30, 2018
INVENTOR(S)      : Chandy et al.

It is certified that error appears in the above-identified patent and that said Letters Patent is hereby corrected as shown below:

In the title delete "PHARMALOGICAL" and insert --PHARMACOLOGICAL--.

Signed and Sealed this
Twenty-fourth Day of April, 2018

Andrei Iancu
*Director of the United States Patent and Trademark Office*

SEQUENCE LISTING

```
<160> NUMBER OF SEQ ID NOS: 7

<210> SEQ ID NO 1
<211> LENGTH: 35
<212> TYPE: PRT
<213> ORGANISM: Unknown
<220> FEATURE:
<223> OTHER INFORMATION: Description of Unknown: Sea anemone ShK toxin
      polypeptide

<400> SEQUENCE: 1

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: p-phospho-Tyr-AEEAc

<400> SEQUENCE: 2

Tyr Arg Ser Cys Ile Asp Thr Ile Pro Lys Ser Arg Cys Thr Ala Phe
1               5                   10                  15

Gln Cys Lys His Ser Met Lys Tyr Arg Leu Ser Phe Cys Arg Lys Thr
            20                  25                  30

Cys Gly Thr Cys
        35

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: p-phospho-Tyr-AEEAc
<220> FEATURE:
<223> OTHER INFORMATION: C-term amide
```

-continued

<400> SEQUENCE: 3

Tyr Arg Ser Cys Ile Asp Thr Ile Pro Lys Ser Arg Cys Thr Ala Phe
1               5                   10                  15

Gln Cys Lys His Ser Met Lys Tyr Arg Leu Ser Phe Cys Arg Lys Thr
            20                  25                  30

Cys Gly Thr Cys
            35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Tyr-AEEAc
<220> FEATURE:
<223> OTHER INFORMATION: C-term amide

<400> SEQUENCE: 4

Tyr Arg Ser Cys Ile Asp Thr Ile Pro Lys Ser Arg Cys Thr Ala Phe
1               5                   10                  15

Gln Cys Lys His Ser Met Lys Tyr Arg Leu Ser Phe Cys Arg Lys Thr
            20                  25                  30

Cys Gly Thr Cys
            35

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term NH2
<220> FEATURE:
<223> OTHER INFORMATION: C-term carboxyl or amide

<400> SEQUENCE: 5

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 6
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term NH2
<220> FEATURE:
<223> OTHER INFORMATION: C-term carboxyl or amide

<400> SEQUENCE: 6

Arg Ser Cys Ile Asp Thr Ile Pro Lys Ser Arg Cys Thr Ala Phe Arg
1               5                   10                  15

```
Cys Lys His Ser Met Lys Tyr Arg Leu Ser Phe Cys Arg Lys Thr Cys
            20                  25                  30

Gly Thr Cys
        35

<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: p-phospho-Tyr-AEEAc
<220> FEATURE:
<223> OTHER INFORMATION: C-term carboxyl or amide

<400> SEQUENCE: 7

Tyr Arg Ser Cys Ile Asp Thr Ile Pro Lys Ser Arg Cys Thr Ala Phe
1               5                   10                  15

Arg Cys Lys His Ser Met Lys Tyr Arg Leu Ser Phe Cys Arg Lys Thr
            20                  25                  30

Cys Gly Thr Cys
        35
```